United States Patent
Spits

[19]

[11] Patent Number: 6,095,994

[45] Date of Patent: Aug. 1, 2000

[54] ORTHESIS FOR THE CARPAL TUNNEL SYNDROME

[75] Inventor: Marc Spits, Achel, Belgium

[73] Assignee: World Health Club S.A., Luxembourg

[21] Appl. No.: 09/187,822

[22] Filed: Nov. 6, 1998

[30] Foreign Application Priority Data

Nov. 6, 1997 [NL] Netherlands ............................ 1007459

[51] Int. Cl.$^7$ ............................... A61F 5/00; A61F 13/00
[52] U.S. Cl. .................................. 602/22; 602/5; 602/20; 602/21; 602/64
[58] Field of Search ................................... 602/5, 20, 21, 602/16, 22, 6, 32, 36, 60, 61, 62; 473/62, 61, 213, 212, 464, FOR 115; 273/189 A

[56] References Cited

U.S. PATENT DOCUMENTS 3,663,334   5/1972   Mueller-Tamm et al. .
3,769,970  11/1973   Swanson .
4,790,301  12/1988   Silfverskiold ............................. 602/22
4,941,460   7/1990   Working .

FOREIGN PATENT DOCUMENTS 486.552    2/1970   Switzerland .
590 664    8/1977   Switzerland .
WO 94/27528  12/1994   WIPO .

*Primary Examiner*—Kim M. Lee
*Attorney, Agent, or Firm*—Quarles & Brady LLP

[57] ABSTRACT

The invention relates to an orthesis for the prevention and/or treatment of carpal tunnel syndrome, comprising a substantially rigid hand fixation brace having two ends, one of which is provided with a part to be fastened to the wrist and underarm while the other is provided with a finger coupling part. The finger coupling part which is formed as a finger supporting brace, preferably only engages the index and middle finger, while the top of the finger supporting brace is open to allow finger movement in the upward direction.

6 Claims, 1 Drawing Sheet

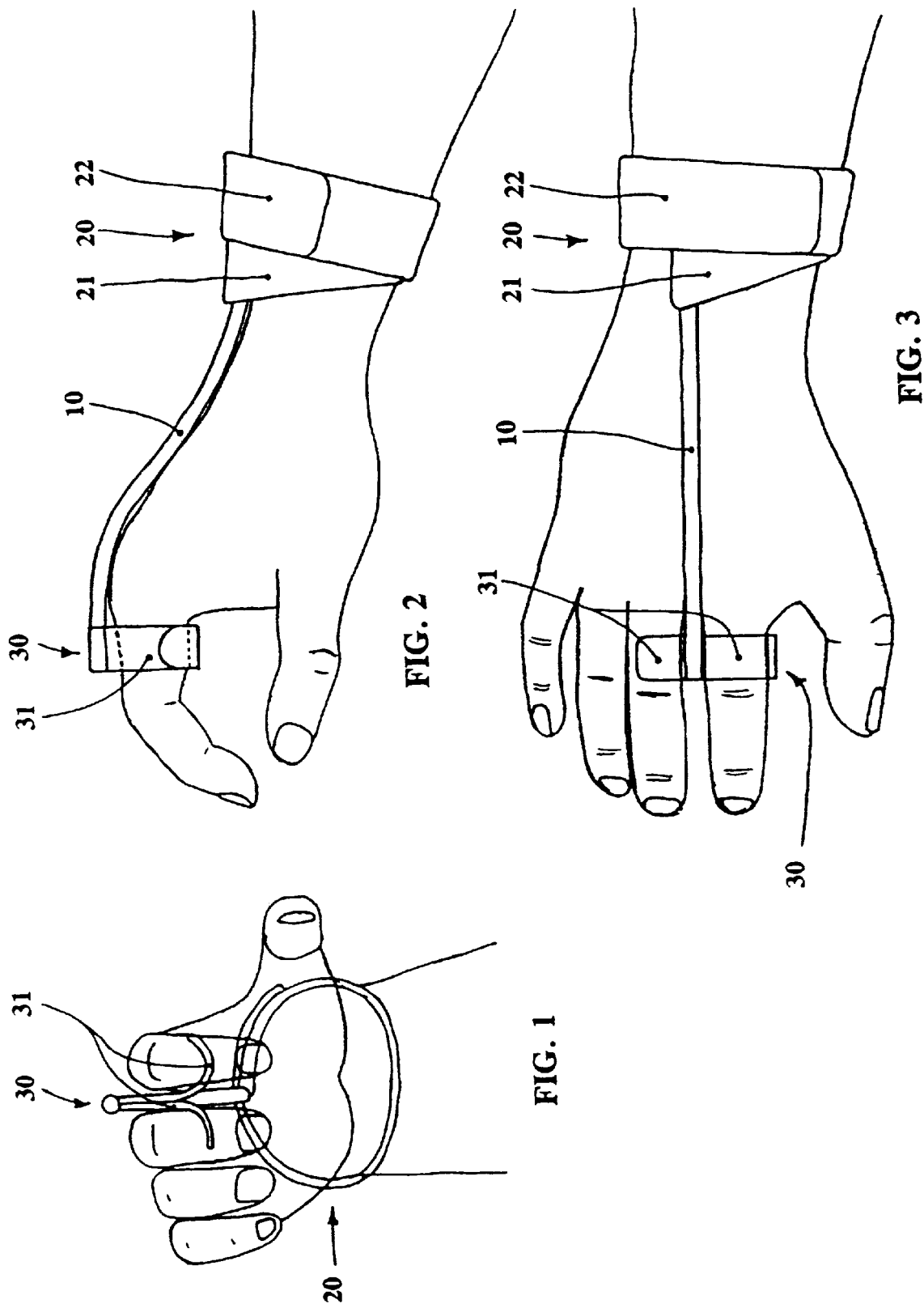

ORTHESIS FOR THE CARPAL TUNNEL SYNDROME

BACKGROUND OF THE INVENTION

Field of the Invention

Brief Summary of the Invention

The present invention relates to an orthesis for the prevention and/or treatment of carpal tunnel syndrome.

Due to excessive use of the fingers and the thumb, for instance when making gripping movements or when typing, the nerve tendons and flexing tendons that control these finger movements, may become irritated. Such an injury caused by excessive use is also known as RSI (Repetitive Strain Injury). At the base of the hand palm, nerve tendons and flexing tendons of the fingers run through a tunnel, the carpal tunnel, which has a length of approximately 2 cm, and is defined at the dorsal side by bone and at the palmar side by a tendon plate. The irritation of the nerve tendons and flexing tendons may cause swelling of the tendon sheaths, thereby pinching the nerves in the carpal tunnel which in turn interferes with the functionality of the tendons. The resulting pain and unusual feeling in the hand palm and fingers caused by this irritation of the tendons at the base of the hand palm are known as the carpal tunnel syndrome.

Naturally, it is preferable to prevent the occurrence of carpal tunnel syndrome. Very often, when a person does suffer from such symptoms, a long period of absolute rest is prescribed, which in terms of working hours and loss thereof, is very costly.

A very drastic treatment is the operative splitting of the tendon plate of the carpal tunnel, to relieve the pressure on the tendons. However, this is rather a major and complicated operation without the guarantee of improvement.

Another possible treatment is the application of a splint to the wrist and hand palm. This treatment, together with a finger-less glove made of elastic material, is known from WO-94/27528, but only partly prevents the tendon's movement in the carpal tunnel.

The object of the invention is to maximally reduce the movements of the tendons in the carpal tunnel in order to prevent or treat carpal tunnel syndrome. To this end the orthesis according to the invention comprises a substantially rigid hand fixation brace having two ends, one of which is provided with a part to be fastened to the wrist and underarm while the other is provided with a finger coupling part.

Due to its uncomplicated construction, the manufacture of such an orthesis is simple, and due to its size, a modest amount of material is required, making the orthesis attractive from an economic point of view.

In a favourable embodiment, the finger coupling part only engages the index and middle finger. From a functional viewpoint these are the most important fingers. Restricting the movement of these fingers almost completely reduces the tendon movement. Therefore the design of the orthesis may be extremely compact. This further increases the applicability and further simplifies manufacture.

Preferably the finger coupling part is formed as a finger supporting brace, which is an effective and simple manner of forming a link with the fingers.

In a preferred embodiment the top of the finger supporting brace is open to allow finger movement in the upward direction. The finger brace now only restricts the downward movement of the fingers. This results in a substantially maximal reduction of the tendon movement, without unduly restricting the use of the hand. Although this prevents gripping, it is still possible to operate the keyboard. This makes the orthesis according to the invention very user-friendly.

Optionally the part to be fastened to the wrist comprises a brace to be fitted around the wrist, which in cross section is a substantially half-round or half-oval brace and, attached to the brace, a band or strap for fastening. In another embodiment the part to be fastened to the wrist comprises a curved plate to be fitted on the wrist and, attached to the plate, a band or strap for fastening. These are simple and effective ways of providing a fastening around the wrist and/or underarm.

The band or strap for fastening is preferably elastic, which makes the orthesis more comfortable in wear and use.

Furthermore, the band or strap is preferably secured by means of Velcro fastening. This provides a secure fastening which is easily adaptable to the size of the user's wrist or underarm.

In a preferred embodiment the supporting parts of the orthesis are made in one piece. This simplifies manufacture and results in a smooth orthesis without any projections that could irritate the hand.

BRIEF DESCRIPTION OF THE DRAWINGS

The invention will now be explained with reference to the accompanying drawings, in which identical reference numbers indicate similar parts and in which:

FIG. 1 is a front view of an orthesis according to the invention;

FIG. 2 is a side view of the orthesis of FIG. 1; and

FIG. 3 is a top view of the orthesis of FIG. 1.

The orthesis shown in the drawings, for the prevention and/or treatment of carpal tunnel syndrome, comprises a hand fixation brace 10, a part 20 to be fastened to the wrist and a finger coupling part 30. The fastening part 20 is located at one end of the hand fixation brace 10 and serves to firmly fix the orthesis to the wrist. The finger coupling part 30 is located at the other end of the hand fixation brace 10. Into said finger coupling part 30 a number of fingers are placed when using the orthesis.

The drawings show an orthesis to be used on the right hand. A similar orthesis can be made for the left hand and an orthesis that may be used on both hands is equally well possible.

When the orthesis is fitted, bending and rotating movements of the hand are prevented and the hand is fixed in a position determined by the form of the orthesis. To a large extent this prevents the movement of the tendons through the carpal tunnel. At the same time the hand's gripping movements are hindered, which further reduces the movements of the tendons.

The finger coupling part 30 shown in the Figures, comprises a finger supporting brace consisting of two finger braces 31, as can be best seen in FIG. 1. This finger supporting brace accommodates the index and middle finger. From a functional viewpoint these are the most important fingers and their fixation results in a further reduction of the movements of the tendons in the carpal tunnel. The movements of the other fingers are now also more or less automatically restricted.

At the top, the finger braces 31 are an upwardly curved open arc to allow the fingers to move in the upward direction. In this way the hand retains a great deal of its functionality. For instance, it is possible to type while using the orthesis. The likelihood of sustaining the carpal tunnel syndrome with this kind of occupation is considerable. However, the use of the orthesis with these occupations is a remarkably effective means of preventing carpal tunnel syndrome of RSI.

The fastening part 20 shown in the figures comprises an in cross section substantially half-oval brace 21 for fitting around the wrist and a fastening band or strap 22 attached to the brace. By means of said band or strap 22 the brace 21 is fixed around the wrist. The band or strap 22 are fitted and fastened in a manner known as such, for instance, by means of Velcro fastening. The comfort in wear can be increased by using an elastic material for the band or strap 22.

In an alternative embodiment the fastening part 20 consists of a plate to be fitted on the wrist which plate is fixed into place by means of a band or strap 22 attached to the plate. This band or strap 22 is also fitted and fastened in a manner known as such.

In the embodiment shown, the hand fixation brace 10, the brace 21 and the finger coupling part 30, that is to say the supporting parts of the orthesis, are made in one piece of a metal such as, for example, aluminium or titanium, or of a plastic.

The above-described embodiments are not to be considered as a limitation to the invention. There are various possible embodiments for the orthesis for the prevention and/or treatment of carpal tunnel syndrome, all within the scope of the present invention and the appended claims.

What is claimed is:

1. An orthesis for use on a hand, wrist and fingers in the prevention and treatment of carpal tunnel syndrome, comprising:

a substantially rigid hand fixation brace adapted to extend immediately over the dorsal part of the hand, a part fastenable to the wrist and attached to a first end of said hand fixation brace; and, a finger coupling part attached to a distal end of said hand fixation brace opposing said first end, said finger coupling part consisting of two finger braces adapted to support the fingers; said finger braces immediately extending downwardly from said hand fixation brace and adapted to extend through adjacent fingers of the hand, said finger braces including a transverse portion upon which the adjacent fingers are supported, said finger brace being an upwardly curved open arc to allow movement of the adjacent fingers in an upward direction.

2. The orthesis according to claim 1, wherein the finger coupling part only supports the index and middle finger.

3. The orthesis according to claim 1, wherein the hand fixation brace is curved upward thereby extending the dorsal part of the hand slightly upward when the orthesis is in use.

4. The orthesis according to claim 1, wherein the part to be fastened to the wrist comprises a brace to be fitted around the wrist, which in cross section is at least one of a substantially half-oval brace, and attached to the brace, at least one of a band and a strap for fastening.

5. The orthesis according to claim 4, wherein at least one of the band and the strap is secured by synthetic hook and loop fastener materials which adhere when pressed together.

6. The orthesis according to claim 1, wherein the supporting parts are made in one piece.

* * * * *

UNITED STATES PATENT AND TRADEMARK OFFICE
CERTIFICATE OF CORRECTION

| | |
|---|---|
| PATENT NO. | : 6,095,994 |
| DATED | : August 1, 2000 |
| INVENTOR(S) | : Marc Spits |

It is certified that error appears in the above-identified patent and that said Letters Patent is hereby corrected as shown below:

<u>Column 1,</u>
Immediately before line 7, remove "Brief Summary of the Invention"
Between lines 11 and 12, insert -- Brief Summary of the Invention --

Signed and Sealed this

Fifth Day of March, 2002

*Attest:*

*Attesting Officer*

JAMES E. ROGAN
*Director of the United States Patent and Trademark Office*